US012571793B2

(12) United States Patent
Matsumoto et al.

(10) Patent No.: US 12,571,793 B2
(45) Date of Patent: Mar. 10, 2026

(54) METHOD FOR EVALUATING BIOFILM FORMATION, AND INVERTEBRATE FOR USE IN EVALUATING BIOFILM FORMATION

(71) Applicant: MEIJI PHARMACEUTICAL UNIVERSITY, Tokyo (JP)

(72) Inventors: Yasuhiko Matsumoto, Tokyo (JP); Takashi Sugita, Tokyo (JP)

(73) Assignee: MEIJI PHARMACEUTICAL UNIVERSITY, Tokyo (JP)

( * ) Notice: Subject to any disclaimer, the term of this patent is extended or adjusted under 35 U.S.C. 154(b) by 0 days.

(21) Appl. No.: 17/802,231

(22) PCT Filed: Feb. 22, 2021

(86) PCT No.: PCT/JP2021/006609
§ 371 (c)(1),
(2) Date: Aug. 25, 2022

(87) PCT Pub. No.: WO2021/172266
PCT Pub. Date: Sep. 2, 2021

(65) Prior Publication Data
US 2023/0078234 A1      Mar. 16, 2023

(30) Foreign Application Priority Data
Feb. 26, 2020    (JP) ................................ 2020-030748

(51) Int. Cl.
*G01N 3/50* (2006.01)
*A01K 67/35* (2025.01)
*G01N 33/50* (2006.01)

(52) U.S. Cl.
CPC ......... *G01N 33/5085* (2013.01); *A01K 67/35* (2025.01); *A01K 2227/703* (2013.01); *G01N 2333/40* (2013.01)

(58) Field of Classification Search
CPC .......... G01N 33/5085; G01N 2333/40; A61K 67/04; A61K 2227/703
See application file for complete search history.

(56) References Cited

U.S. PATENT DOCUMENTS

| | | |
|---|---|---|
| 2015/0111813 A1 | 4/2015 | Schuch et al. |
| 2015/0132796 A1 | 5/2015 | Boels et al. |
| 2019/0218953 A1 | 7/2019 | Bowler et al. |
| 2019/0282673 A1 | 9/2019 | Channabasappa et al. |

FOREIGN PATENT DOCUMENTS

| | | |
|---|---|---|
| CN | 108330157 A | 7/2018 |
| EP | 2 537 601 A1 | 12/2012 |
| JP | 2018-87242 A | 6/2018 |
| JP | 2018-189655 A | 11/2018 |

OTHER PUBLICATIONS

Hamamoto et al. (Antimicrobial Agents and Chemotherapy vol. 48 No. 3, pp. 774-779).*
Zufferey et al. (Journal of Clinical Microbiology, vol. 26 No. 2, pp. 175-177). (Year: 1988).*
Chinese Office Action and Search Report for Chinese Application No. 202180016573.1, dated Mar. 3, 2025, with English translation.
Sasaki et al., "Enniatins from a marine-derived fungus *Fusarium* sp. inhibit biofilm formation by the pathogenic fungus *Candida albicans*," Journal of Natural Medicines, vol. 77, 2023, pp. 455-463.
Japanese Office Action for corresponding Japanese Application No. 2022-503601, dated Sep. 26, 2024, with an English translation.
Campos-Silva, et al., "Alternative method in Galleria mellonella larvae to study biofilm infection and treatment", Microbial Pathogenesis, Sep. 20, 2019, vol. 137, Article 103756, pp. 1-5.
International Search Report (PCT/ISA/210) issued in PCT/JP2021/006609 mailed on Apr. 13, 2021.
Matsumoto et al., "Development of an in vivo evaluation system for biofilm formation by Candida albicans on the surface of medical device materials", Japanese Journal of Medical Mycology, Sep. 2020, vol. 61, Supplement 1, p. 85.
Matsumoto et al., "Evaluating Candida albicans biofilm formation in silkworms", Medical Mycology, Aug. 11, 2020, vol. 59, No. 2, pp. 201-205.
Written Opinion (PCT/ISA/237) issued in PCT/JP2021/006609 mailed on Apr. 13, 2021.
Yonemoto et al., "Redundant and Distinct Roles of Secreted Protein Eap and Cell Wall-Anchored Protein SasG in Biofilm Formation and Pathogenicity of *Staphylococcus aureus*", Infection and Immunity, Mar. 25, 2019, vol. 87, No. 4, Article e00894-18, pp. 1-15.
Chinese Office Action for counterpart Chinese Application No. 202180016573.1, dated Jun. 18, 2025, with English translation.
Chinese Office Action for Chinese Application No. 202180016573.1, dated Jul. 28, 2025, with English translation.

* cited by examiner

*Primary Examiner* — Robert A Zeman
(74) *Attorney, Agent, or Firm* — Birch, Stewart, Kolasch & Birch, LLP

(57) ABSTRACT

A method for evaluating biofilm formation on a medical device material in vivo using an invertebrate includes: a step of inserting the medical device material between a hypodermal portion and an intestinal tract of an invertebrate, a step of extracting the medical device material from the invertebrate, and a step of evaluating biofilm formation on the surface of the medical device material; the invertebrate is for use in this evaluation of the biofilm formation.

8 Claims, 16 Drawing Sheets

(a)                                                    (b)

(a)

Control

C. albicans
(SC5314)

(b)

Control

C. albicans
(SC5314)

(a)

Saline

C. albicans (b)

Saline

C. albicans

METHOD FOR EVALUATING BIOFILM FORMATION, AND INVERTEBRATE FOR USE IN EVALUATING BIOFILM FORMATION

TECHNICAL FIELD

The presently disclosed subject matter relates to a method for evaluating biofilm formation and an invertebrate for use in evaluating biofilm formation, and relates particularly to a method of evaluating in vivo biofilm formation using an invertebrate and an invertebrate for use in evaluating the biofilm formation.

The presently disclosed subject matter relates to a patent application to which Article 17 of Industrial Technology Enhancement Act is applied for the research and development of "Research on pathogenic elucidation, epidemiology, diagnostic method, and controlling method of invasive yeast infectious diseases" in accordance with "Research Program for Practical Use against Infectious Diseases: Research Program for Promoting Development of Innovative Medicines and the Like against Emerging and Reemerging Infectious Diseases" entrusted by Japan Agency for Medical Research and Development in the fiscal year 2020.

BACKGROUND ART

For example, *Candida albicans* (hereinafter abbreviated as *C. albicans*) is a pathogenic fungus that causes blood infectious diseases, and causes systemic critical mycosis in immunodeficient patients. If *C. albicans* forms biofilms on a surface of a catheter, that is an example of a medical device in patients in which the catheter is inserted, antimicrobial drugs (antifungal drugs) are hardly effective, and the medical treatment is difficult. It is therefore believed that the establishment of a method for suppressing biofilm formation by fungi contributes to the prevention and the treatment of blood infectious diseases and the like caused by fungi.

The environments in hosts affect the biofilm formation of *C. albicans* greatly, and not only nutrient components such as glucose and amino acids but also host cells and proteins are important constituent elements of biofilms by *C. albicans*. It is clear from comprehensive gene expression analysis that the gene expression patterns of *C. albicans* at the time of biofilm formation in vitro and in vivo are different. Experiment models for evaluating the biofilm formation of *C. albicans* in vivo are therefore very important.

For example, the Patent Literature 1 describes an evaluation method using mice for evaluating lysins used for prevention of biofilm formation on a catheter, destruction of the biofilms, and treatment of the biofilms.

CITATION LIST

Patent Literature

{PTL 1}: Japanese Patent Application Laid-Open No. 2018-087242

SUMMARY OF INVENTION

Technical Problem

Tests using mice, rats, or the like, which are mammals, imposed burdens such as ethical problems, breeding cost, and breeding spaces, and it was difficult to perform experiments using many animal individuals due to the securing of drugs to be administered, or the like. Tests using mice and rats needed operations accompanied with anesthesia at the time of experiments, and the work was complicated.

The presently disclosed subject matter has been completed in view of such a situation. An object thereof is to provide a method of evaluating biofilm formation on a medical device material in vivo using an invertebrate and an invertebrate for use in evaluating biofilm formation, wherein it is advantageous to use the invertebrate since the ethical problem is small as compared with a mouse, and since an experiment using many individuals can be performed.

Solution to Problem

In order to achieve the object of the presently disclosed subject matter, a method for evaluating biofilm formation according to the presently disclosed subject matter is a method for evaluating biofilm formation on a medical device material using an invertebrate, and includes a step of inserting the medical device material between a hypodermal portion and an intestinal tract of the invertebrate, a step of extracting the medical device material from the invertebrate, and a step of evaluating biofilm formation on a surface of the medical device material.

One aspect of the presently disclosed subject matter preferably includes a step of infecting the invertebrate in which the medical device material has been inserted with a fungus before the step of extracting the medical device material.

One aspect of the presently disclosed subject matter preferably includes a step of administering an antimicrobial drug to the invertebrate, and the step of evaluating the biofilm formation preferably includes evaluating the antimicrobial drug.

In one aspect of the presently disclosed subject matter, the medical device material is preferably kept in the invertebrate for a predetermined period of time after the medical device material has been inserted in the invertebrate.

In one aspect of the presently disclosed subject matter, the medical device material is preferably a catheter.

In one form of the presently disclosed subject matter, the invertebrate is preferably a larva of a Lepidoptera insect.

In one form of the presently disclosed subject matter, the invertebrate is preferably a silkworm.

In one form of the presently disclosed subject matter, the silkworm is preferably a fifth instar silkworm.

In one form of the presently disclosed subject matter, a thickness of the medical device material is preferably ⅓ or less of a trunk thickness of the silkworm.

In one aspect of the presently disclosed subject matter, the medical device material is preferably inserted through an abdomen of the silkworm in the step of inserting the medical device material.

In one aspect of the presently disclosed subject matter, the medical device material is preferably inserted through near a crescent marking on the abdomen of the silkworm in the step of inserting the medical device material.

In one aspect of the presently disclosed subject matter, the medical device material is preferably inserted along the intestinal tract of the silkworm in the step of inserting the medical device material.

In one aspect of the presently disclosed subject matter, the step of evaluating the biofilm formation is preferably performed by staining.

In order to achieve the object of the presently disclosed subject matter, the invertebrate according to the presently disclosed subject matter is an invertebrate for use in evaluating biofilm formation, wherein the invertebrate is used for evaluating biofilm formation on a surface of a medical device material in vivo with the medical device material inserted between a hypodermal portion and an intestinal tract.

Advantageous Effects of Invention

According to the presently disclosed subject matter, the evaluation of biofilm formation in vivo using an invertebrate can be performed, wherein it is advantageous to use the invertebrate since the ethical problem is small, and since an experiment using many individuals can be performed.

DESCRIPTION OF EMBODIMENTS

Figure 1:
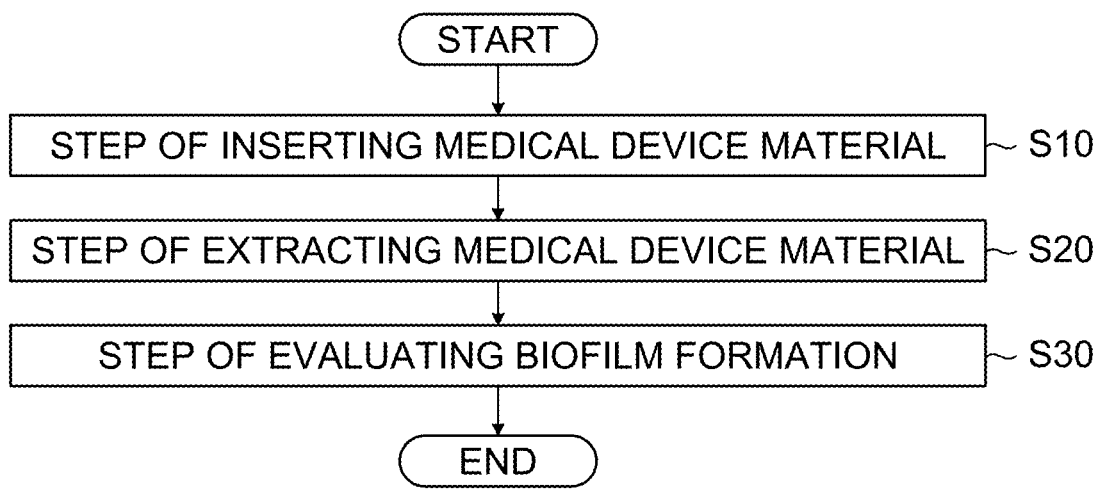
FIG. 1 is a flow chart illustrating a method for evaluating biofilm formation.
Figure 2:
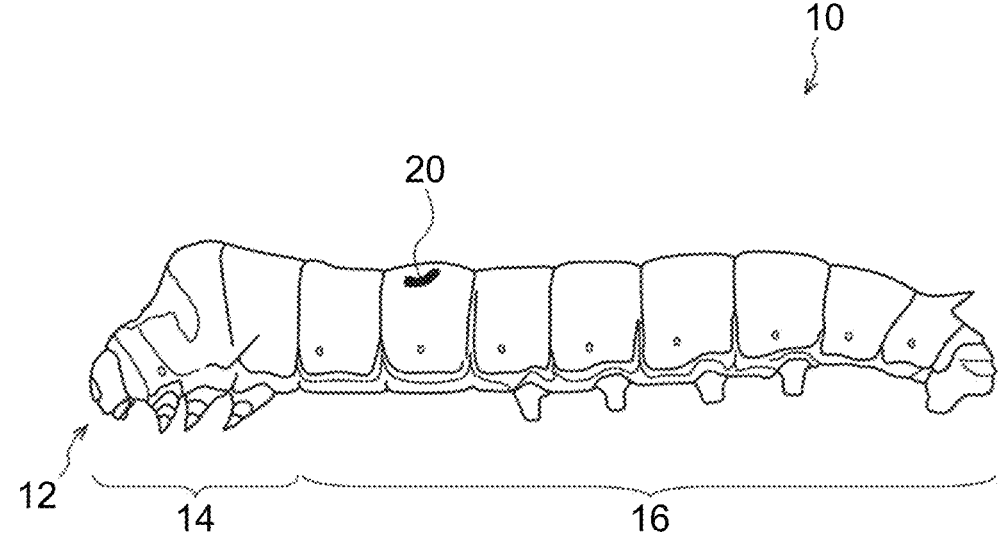
FIG. 2 is a figure of a silkworm.
Figure 3:
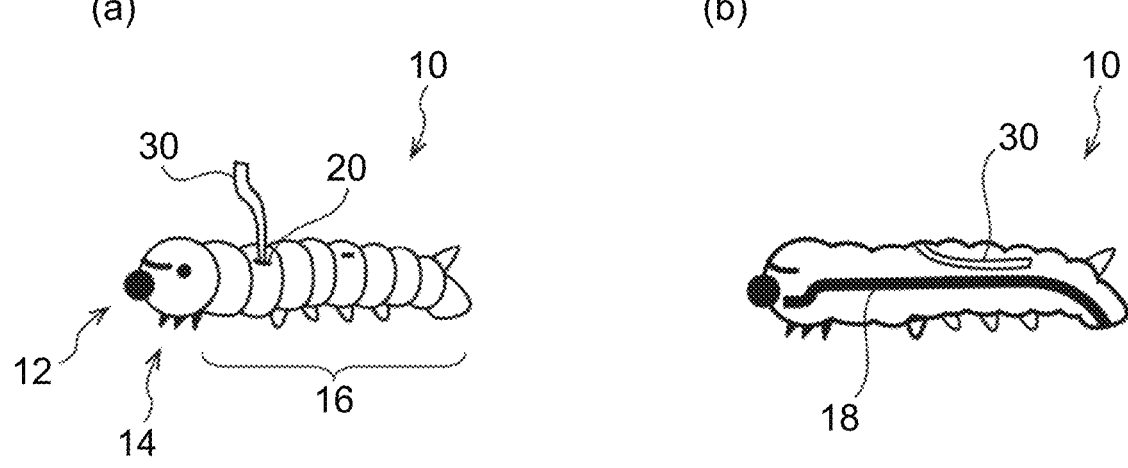
FIG. 3 is figures describing a step of inserting a medical device material.

Hereinafter, preferable embodiments of a method for evaluating biofilm formation and an invertebrate according to the presently disclosed subject matter will be described in accordance with the attached drawings.
«Method for Evaluating Biofilm Formation»
FIG. 1 is a flow chart illustrating a method for evaluating biofilm formation. The method for evaluating biofilm formation of the present embodiment is a method for evaluating biofilm formation on a medical device material using an invertebrate, and has a step of inserting a medical device material between a hypodermal portion and an intestinal tract of an invertebrate (step S10), a step of extracting the medical device material from the invertebrate (step S20), and a step of evaluating biofilm formation on the surface of the medical device material (step S30).
[Step of Inserting Medical Device Material] (Step S10)
The step of inserting the medical device material includes a step of inserting a medical device material between a hypodermal portion and the intestinal tract of an invertebrate. Hereinafter, a silkworm will be exemplified and described as the invertebrate.
FIG. 2 is a figure of a silkworm. The (a) portion of FIG. 3 is a figure in which the medical device material is inserted in a silkworm, and the (b) portion of FIG. 3 is a figure of the body inside of the silkworm in which the medical device material is inserted.
As illustrated in FIG. 2, a silkworm 10 includes a head 12, a thorax 14, and an abdomen 16. The body includes 13 segments, a portion having three segments connected to the head 12, which is the front end, is referred to as the thorax 14, and ten segments therebehind are referred to as the abdomen 16. It is an intestinal tract 18, which is an alimentary canal, that occupies most of the body inside. The intestinal tract 18 is roughly divided into a foregut, a midgut, and a hindgut (not illustrated).

When the medical device material 30 is inserted in the body of the silkworm 10, the medical device material 30 is preferably inserted through the abdomen 16 of the silkworm and more preferably inserted through near a crescent marking 20, which is located on the second segment from the thorax 14 side of the abdomen 16. When the medical device material 30 is inserted in the silkworm 10, it is preferable to make a hole in a place in which the medical device material 30 is inserted with a needle for injection or the like. The medical device material 30 can be inserted along the intestinal tract 18 between the hypodermal portion and the intestinal tract 18 by inserting the medical device material 30 through near a crescent marking 20 along the hypodermal portion. Biofilm formation on the medical device material 30 in vivo can be appropriately evaluated by preventing the insertion of the medical device material 30 into the intestinal tract 18.

After the medical device material 30 is inserted in the silkworm, the medical device material 30 is kept in the silkworm 10 for a predetermined period of time. The biofilm formation in the living body (in vivo) can be evaluated thereby. Although time to keep the medical device material 30 in the silkworm 10 can be suitably changed depending on the experimental method and the evaluation method, the time is preferably within time for which the silkworm is not killed by experimental treatments such as the inoculation of a fungus and the administration of a drug. It is specifically preferable that the time be 24 hours or less.
<Invertebrate>
Although the invertebrate to be used in the present embodiment is not limited to a silkworm, and can be suitably selected depending on the object. The invertebrate is preferably a larva of an insect from the viewpoint of convenience of handling. A Larva of a Lepidoptera insect such as a butterfly or a moth is in the shape of a caterpillar, and is further preferable in that drugs are accurately administered by injection or the like.

As such a larva, a silkworm is further preferable in view of the following points.
(1) Silkworms can be easily obtained.
(2) A method for breeding silkworms has already been established, and silkworms are bred conveniently.
(3) The property of silkworms being similar to Mammalia such as humans in internal organs and organs has been found to some degree by conventional investigation.
(4) Genetic lines of silkworms have been established, and the genetic homogeneity has been successfully maintained.
(5) Since silkworms are comparatively large, move slowly, and are substantially hairless, silkworms can be injected quantitatively, and drugs are easily administered to silkworms.
(6) Silkworms are low-priced as compared with mice, rats, or the like, many individuals can be bred in a small space, and ethical problems are also few.
(7) Even if only a small amount of a test substance is present, the test substance can be evaluated.
(8) Individuals in the same states are easily collected by unifying the instars, or the like.
(9) Since silkworms do not escape, or cannot survive in nature, there is no danger of biological hazard (biohazard).

Silkworms have a simple caterpillar shape, which specializes in nutritional supplementation, and have instar periods defined by several ecdysis. The growth states of individuals for use in tests can therefore be accurately unified by unifying the instar periods. The most suitable instar period can also be selected depending on the object. Silkworms have many excellent characteristics of silkworms being easily bred, and drugs or the like being easily injected thereinto due to slow movement thereof as test animals.

Although the size and the instar number of a silkworm are not particularly limited, a third instar or older silkworm is preferable, and a fifth instar silkworm is more preferable from the viewpoints of the stable growth state and operations such as the injection of a drug, and the insertion and extraction of the medical device material.

<Medical Device Material>

As the medical device material to be used in the present embodiment, a material for medical devices used by making the medical devices indwell in the living body can be used. Examples of the medical devices include catheters and artificial joints. Polyurethane can be used as a material of catheters. Besides, silicon, polyethylene, polypropylene, polystyrene, and the like can be used as materials of medical devices.

When an experiment is performed using a catheter as the medical device in a mouse, rat or the like, a catheter is needed to be inserted in a blood vessel of the mouse, rat or the like. Therefore, such the experiment requires a hollow tubular catheter with a size able to be inserted in the blood vessel of the mouse, rat or the like. According to the present embodiment, since an invertebrate is used, the medical device material only has to be inserted in a humor of an invertebrate, and the medical device material does not need to be made hollow and tubular for passing blood therethrough. Therefore, the provision of the medical device material can be simplified. In the evaluation of biofilm formation mentioned below, the biofilm formation can be evaluated by eluting the biofilm formed on the surface of the medical device material with a chemical. In the case of the hollow tubular catheter, it is difficult to take out liquid in the hollow tubular due to capillarity. Therefore, it may be difficult to analyze the biofilms formed in the hollow tubular. By using the invertebrate, the biofilm formed on the surface of the medical device material can be quantitatively evaluated.

It is preferable that the thickness of the medical device material be ⅕ or less of the trunk thickness of the silkworm. The medical device material can be installed at a predetermined position in the silkworm body by adjusting the thickness of the medical device material to this range.

[Step of Extracting Medical Device Material] (Step S20)

The medical device material 30 is extracted from silkworm 10 after the elapse of a predetermined period of time. The method for extracting the medical device material 30 is not particularly limited, and can be performed by pull out the medical device material 30 from the silkworm 10.

[Step of Evaluating Biofilm Formation] (Step S30)

The step of evaluates biofilm formation includes a step of analyzing the biofilm formed on the surface of the medical device material 30 extracted from the silkworm 10 and evaluating biofilm formation. The biofilm formation can be evaluated by staining the biofilms by staining and observing the biofilms under a microscope. The stained biofilms can be quantified by eluting the stained biofilm and measuring the absorbance.

As mentioned above, the insertion of the medical device material 30 in the silkworm 10 is different from the insertion in a rat, a mouse, or the like. The medical device material 30 can be inserted not in blood but between the hypodermal portion and the intestinal tract. The medical device material 30 does not therefore need to be formed into a hollow tubular shape. The biofilms formed on the surface of the medical device material 30 only have to be analyzed, the formed biofilms can be quantified accurately by measuring the absorbance. In a stain solution used for staining, crystal violet can be used, and the absorbance of a solution obtained by eluting the biofilms stained with this crystal violet with an aqueous acetic acid solution is measured. A wavelength of 590 nm can be used as the wavelength at which the absorbance is measured.

OTHER EMBODIMENTS

Figure 4:
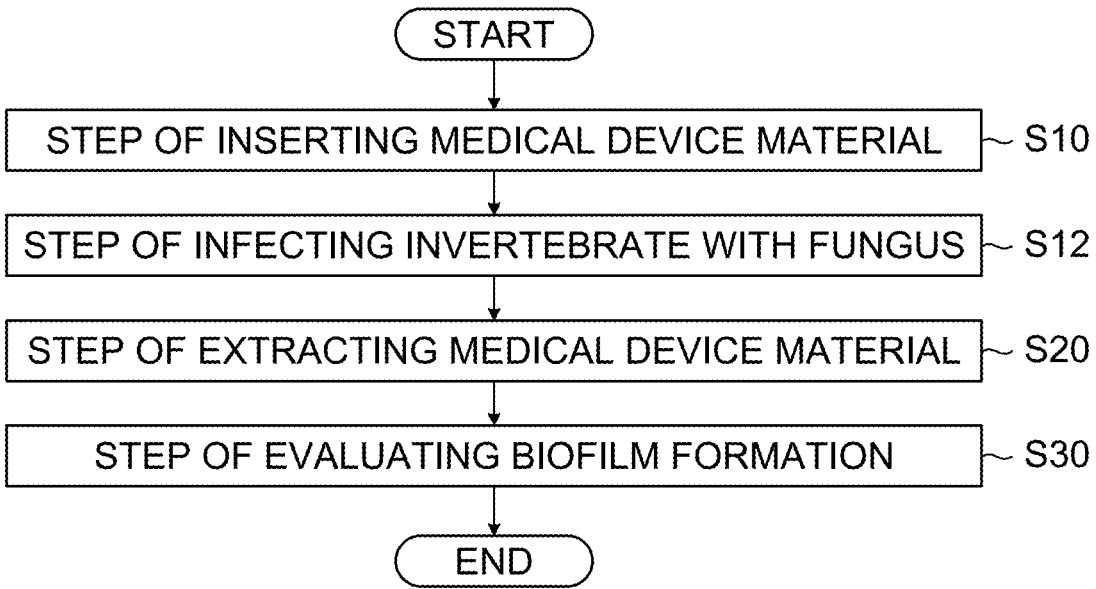
FIG. 4 is a flow chart illustrating a method for evaluating biofilm formation of another embodiment.

FIG. 4 is a flow chart illustrating a method for evaluating biofilm formation of another embodiment. The method for evaluating biofilm formation of the embodiment illustrated in FIG. 4 is different from the method of evaluating biofilm formation illustrated in FIG. 1 in whether the method has a step of infecting the invertebrate with a fungus (step S12).

[Step of Infecting Invertebrate with Fungus] (Step S12)

The step of infecting the invertebrate with the fungus includes a step of inoculating the silkworm 10 with the fungus and infecting the silkworm 10 with the fungus after the step of inserting the medical device material 30 (step S10). After the insertion of the medical device material 30, the biofilm formation on the medical device material 30 can be promoted by inoculating the silkworm 10 with the fungus. It can be evaluated whether the inoculated fungus forms biofilms.

As the fungus, for example, *C. albicans, Staphylococcus aureus, Candida glabrata*, or the like can be inoculated. and a fungus for evaluating whether biofilms are formed can be inoculated.

Although the method for inoculating a fungus is not particularly limited, the method is performed by administering a suspension of the fungus in physiological saline solution to the humor of the silkworm 10 using a syringe. Although the concentration at which the fungus is inoculated can be suitably changed depending on the object and the method of the experiment, it is preferable that the concentration be a concentration at which the silkworm does not die during the experiment.

The step of infecting the silkworm with the fungus (step S12) is performed, the step of extracting the medical device material (step S20) and the step of evaluating the biofilm formation (step S30) are then performed, and the biofilm formation is evaluated in the same way as in the method for evaluating biofilm formation illustrated in FIG. 1.

Figure 5:
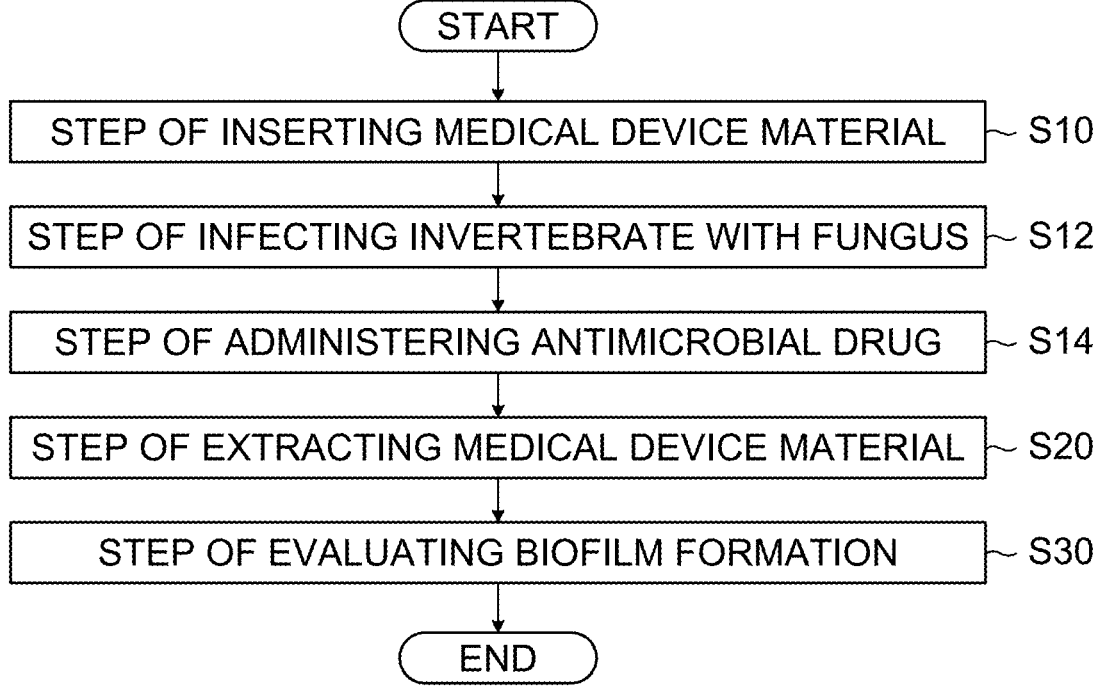
FIG. 5 is a flow chart illustrating a method for evaluating biofilm formation of yet another embodiment.

FIG. 5 is a flow chart illustrating a method for evaluating biofilm formation of yet another embodiment. The method for evaluating biofilm formation of the embodiment illustrated in FIG. 5 is different from the method for evaluating biofilm formation illustrated in FIG. 4 in whether the method has a step of administering an antimicrobial drug (step S14).

[Step of Administering Antimicrobial Drug] (Step S14)

The step of administering an antimicrobial drug includes a step of administering an antimicrobial drug to the silkworm 10 after the step of infecting the silkworm with the fungus (step S12). The effect of the antimicrobial drug can be confirmed by administering the antimicrobial drug.

Although the method for administering an antimicrobial drug is not particularly limited, the method can be performed by administering an antimicrobial drug prepared at a predetermined concentration to a humor. The concentration and the dose can be suitably changed depending on the object and the method of the experiment.

Time for administering an antimicrobial drug can also be suitably changed depending on the object and method of the experiment. For example, the effect of the antimicrobial drug before biofilms are formed on the medical device material can be confirmed by administering an antimicrobial drug immediately after the fungus is administered. The effect of the antimicrobial drug after biofilms are formed can be confirmed by administering the antimicrobial drug a predetermined period of time after the inoculation of the fungus (after biofilm formation). Anti-biofilm compounds having different action mechanisms of the destruction of biofilms after biofilms are formed unlike the conventional antimicrobial drugs can be identified thereby. For example, the effect of the antimicrobial drug after biofilm formation can be confirmed by administering the antimicrobial drug 18 hours after the inoculation of the fungus.

Examples of the antifungal drug include amphotericin B, fluconazole, and micafungin.

The step of administering the antimicrobial drug (step S14) is performed, the step extracting the medical device material (step S20) and the step of evaluating biofilm formation (step S30) are then performed. And, the biofilm formation is evaluated in the same way as in the method for evaluating biofilm formation illustrated in FIG. 1.

As described above, biofilm formation on the medical device material in vivo can be evaluated using the invertebrate according to the present embodiment. The invertebrate can be used for evaluating biofilm formation on the medical device material in vivo.

Example 1

Hereinafter, the presently disclosed subject matter will be described further specifically by giving the Examples. As long as the material, the used amount, the rate, the contents of treatment, the treatment procedure, and the like shown in the following Examples do not deviate from the gist of the presently disclosed subject matter, the material, the used amount, the rate, the contents of treatment, the treatment procedure, and the like can furthermore be suitably changed. Therefore, the scope of the presently disclosed subject matter should not be restrictively interpreted by the specific examples shown below.

(Culture of *C. albicans*)

*C. albicans* (strain SC5314) was applied to YPD agar medium (peptone: 20 g/L, bacto yeast extract: 10 g/L, glucose: 20 g/L, Agar: 15 g/L) and cultured at 37° C., and grew into colonies.

(Breeding of Silkworms)

A method for breeding silkworms was performed according to the method described in Kaito C, et al., Silkworm larvae as an animal model of bacterial infection pathogenic to humans. Microb Pathog 2002; 32: 183-190. The eggs of silkworms were purchased from EHIME SANSYU. The eggs of the silkworms were hatched at 25° C., and Silkmate 2S, which was an artificial feed purchased from EHIME SANSYU, was given. The fifth instar silkworms were used for tests.

[Test Example 1] (Biofilm Formation on Polyurethane Fiber Surface In Vitro)

In order to see whether biofilms were formed on the surface of polyurethane fibers, which were a material for a catheter, biofilm formation was attempted on the polyurethane fiber surface in vitro. The method described in Kurakado S, et al. Association of the hypha-related protein Pra1 and zinc transporter Zrt1 with biofilm formation by the pathogenic yeast *Candida albicans*. Microbiol Immunol 2018; 62: 405-410 was altered, and the altered method was performed as the biofilm formation test.

Polyurethane fibers (thickness: 0.5 mm, rubber gut F046, No. H3) were cut to 2 cm in length, treated with 70% EtOH (ethanol) for 15 minutes, and dried under UV irradiation conditions for 30 minutes. *C. albicans* (strain SC5314) grown on YPD agar medium was scraped off with a platinum loop and inoculated into RPMI 1640 buffered with 165 mM MOPS at $7 \times 10^6$ cells/ml. Some of the polyurethane fibers were added to the medium containing *C. albicans* and subjected to stationary culture at 37° C. for 2 days. RPMI medium containing the others of the polyurethane fibers was used as a control. The test was performed using six samples in each group.

(Quantification of Biofilms)

Biofilms formed on the surface of the polyurethane fibers after the culture were stained with crystal violet, and the biofilms were quantified. The biofilms were stained as follows. Each of the polyurethane fibers were moved to a 1.5-ml tube and washed with 1 ml of distilled water twice. Then, 500 µl of an aqueous 0.1% crystal violet solution was added, and the polyurethane fiber was placed at room temperature for 20 to 60 minutes. The stain solution was discarded, and the polyurethane fiber were washed with 1 ml of distilled water 3 times. The polyurethane fibers were washed with 1 ml of ethanol twice and then air-dried. The polyurethane fibers were observed under a microscope (×10, CH30, Olympus Corporation), and photographs were taken. Then, 500 µl of 33% acetic acid solution was added, and the polyurethane fibers were left to stand at room temperature for 2 hours or more. The absorbance ($OD_{590}$) of the sample to which 500 µl of distilled water was added to adjust the total volume to 1 ml was measured.

Figure 6:
FIG. 6 illustrates results of Test Example 1.
Figure 6:
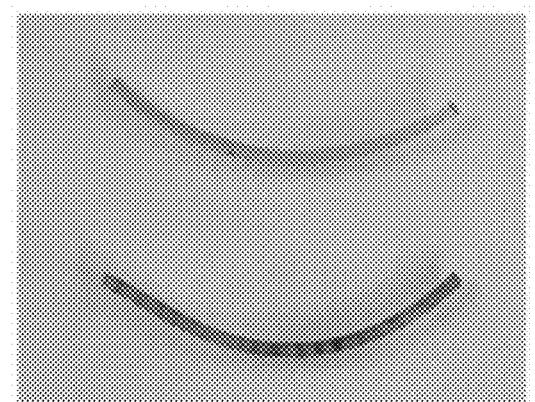
Figure 6:
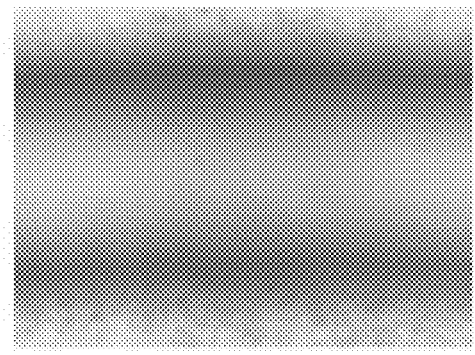
Figure 6:
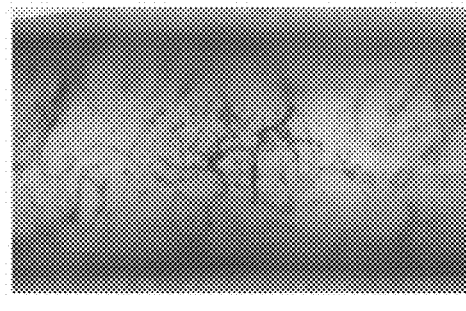
Figure 7:
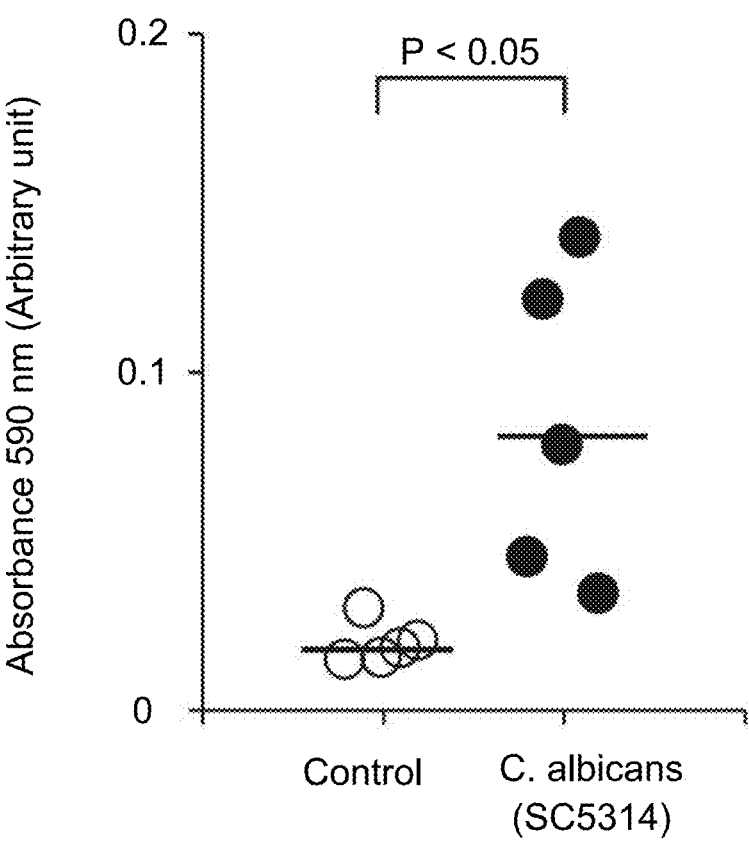
FIG. 7 illustrates the results of Test Example 1.

FIG. 6 and FIG. 7 illustrate the results obtained by forming biofilms on the polyurethane surface in vitro. The (a) portion of FIG. 6 illustrates a photograph after the polyurethane fibers were stained, and the (b) of FIG. 6 illustrates enlarged photographs under a microscope. FIG. 7 illustrates the absorbances of the samples. The absorbance values of the samples were subjected to t-tests (t-examinations). When the P values were 0.05 or less, it was determined that the differences were statistically significant differences.

As illustrated in the (a) portion of FIG. 6, the polyurethane fiber was stained blue in the sample, to which *C. albicans* was added, as compared with the control, to which *C. albicans* was not added. As illustrated in the (b) portion of FIG. 6, an image in which hyphae were formed on the polyurethane fiber surface was observed in the sample, to which *C. albicans* was added. The amounts of the dye adhered to the polyurethane fibers significantly increased by the addition of *C. albicans* from the results of the absorbance illustrated in FIG. 7.

It was confirmed from the above results that *C. albicans* formed biofilms on the polyurethane fiber surface, and it could thus be confirmed that the polyurethane fibers were suitable for use in in vivo animal tests of biofilm formation.

[Test Example 2] (Infection Experiment of Silkworm in which Polyurethane Fiber was Inserted)

Next, the polyurethane fibers were inserted in the bodies of silkworms to examine whether the experiment of infection with *C. albicans* can be performed. A hole was made near a crescent marking on the back of each silkworm with a 27-gauge injection needle, and a 2-cm polyurethane fiber was inserted through the hole. Polyurethane fibers treated and dried by the same method as in Test Example 1 were used as the polyurethane fibers. Among the silkworms in which the polyurethane fibers were inserted, physiological saline solution (saline) was administered to some silkworms, and the other silkworms were inoculated with 50 μl of a suspension of *C. albicans* strain SC5314 ($2 \times 10^7$ cells/ml). Thus, the influence of *C. albicans* inoculation was examined. Further, among silkworms in which the polyurethane fibers were not inserted, physiological saline solution was administered to some silkworms, and the other silkworms were inoculated with *C. albicans*. Thus, the influence of the insertion of the polyurethane fibers was examined. The test was performed using six samples in each group.

Figure 8:
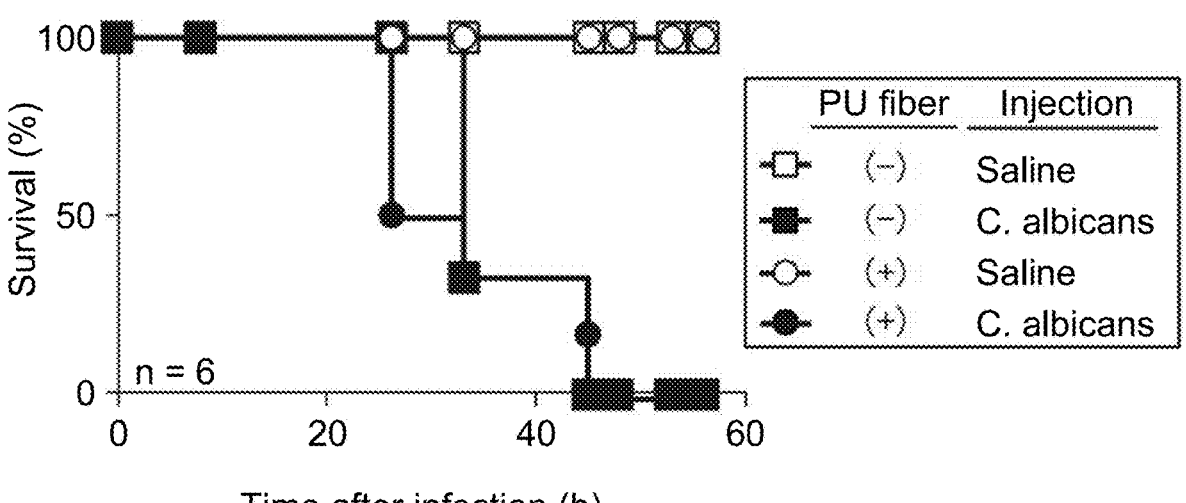
FIG. 8 illustrates results of Test Example 2.

FIG. 8 illustrates the results. Even though the polyurethane fibers were inserted, the silkworms to which physiological saline solution was administered did not die even after 48 hours elapsed. All of the silkworm inoculated with *C. albicans* died within 48 hours regardless of whether the polyurethane fibers were inserted or not. It could be confirmed from the above results that even after the polyurethane fibers were inserted, the silkworms survived for 48 hours or more, and that the experiment of infection with *C. albicans* could be performed under this condition.

[Test Example 3] (In Vivo Silkworm Infection Experiment)

Next, it was examined whether biofilms by *C. albicans* were formed on the surface of the polyurethane fibers in the bodies of silkworms. Silkworms in which the polyurethane fibers were inserted were inoculated with 50 μl of physiological saline solution (saline) or 50 μl of a suspension of *C. albicans* strain SC5314 ($7 \times 10^7$ cells/ml) and bred at 27° C. for 24 hours. The polyurethane fibers were extracted from inside the bodies of the silkworms 24 hours after. The polyurethane fibers were inserted by the same method as in Test Example 2. *C. albicans* was inoculated as follows. *C. albicans* (strain SC5315) that grew on YPD agar medium was scraped off with a platinum loop and suspended in physiological saline solution (0.9% NaCl). A 1-ml tuberculin syringe (Terumo Corporation, Tokyo, Japan) was filled with this suspension of *C. albicans*, and 50 μl of the suspension was administered to the abdominal cavities of the silkworms. The silkworms were bred at 27° C. After 24 hours, the silkworms were placed on ice for 15 minutes, and the polyurethane fibers were extracted from insides the bodies of the anesthetized silkworms. The test was performed using five samples in each group.

Figure 9:
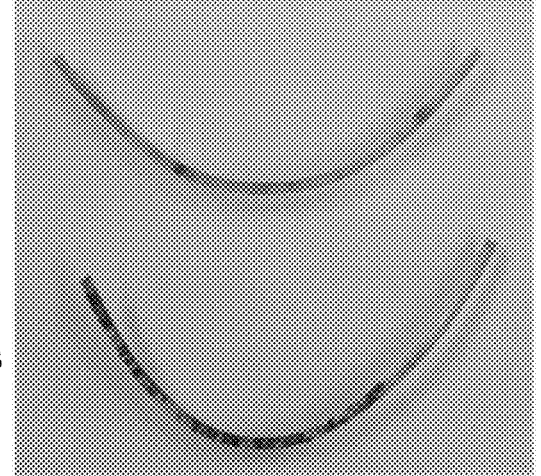
FIG. 9 illustrates results of Test Example 3.
Figure 9:
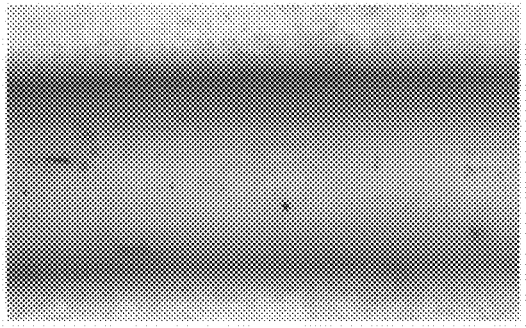
Figure 9:
Figure 10:
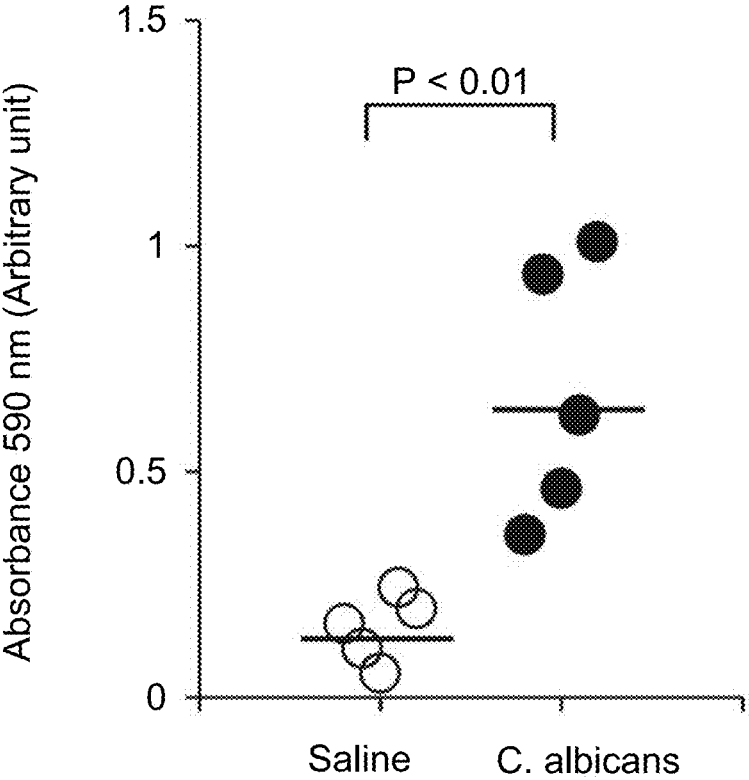
FIG. 10 illustrates the results of Test Example 3.

The extracted polyurethane fibers were stained with crystal violet. FIGS. 9 and 10 illustrate the results. As illustrated in the (a) portion of FIG. 9, the polyurethane fiber was stained bluer when *C. albicans* was inoculated as compared with when physiological saline solution was inoculated into the silkworms. As illustrated in the (b) portion of FIG. 9, an image in which *C. albicans* adhered to the polyurethane fiber surface was confirmed by microscopic observation. Such an image could not be observed when physiological saline solution was inoculated into the silkworm. FIG. 10 is a graph obtained by eluting the dye on the polyurethane fibers with an aqueous 33% acetic acid solution and measuring the absorbances at 590 nm. The amounts of the dye adhered to the polyurethane fibers have significantly increased by the inoculation of *C. albicans* as compared with when physiological saline solution is inoculated into the silkworms.

It was confirmed from the above that *C. albicans* formed biofilms on the polyurethane fiber surface in the bodies of the silkworms.

[Test Example 4] (Suppression Effect of Antifungal Drugs on Biofilm Formation)

Figure 11:
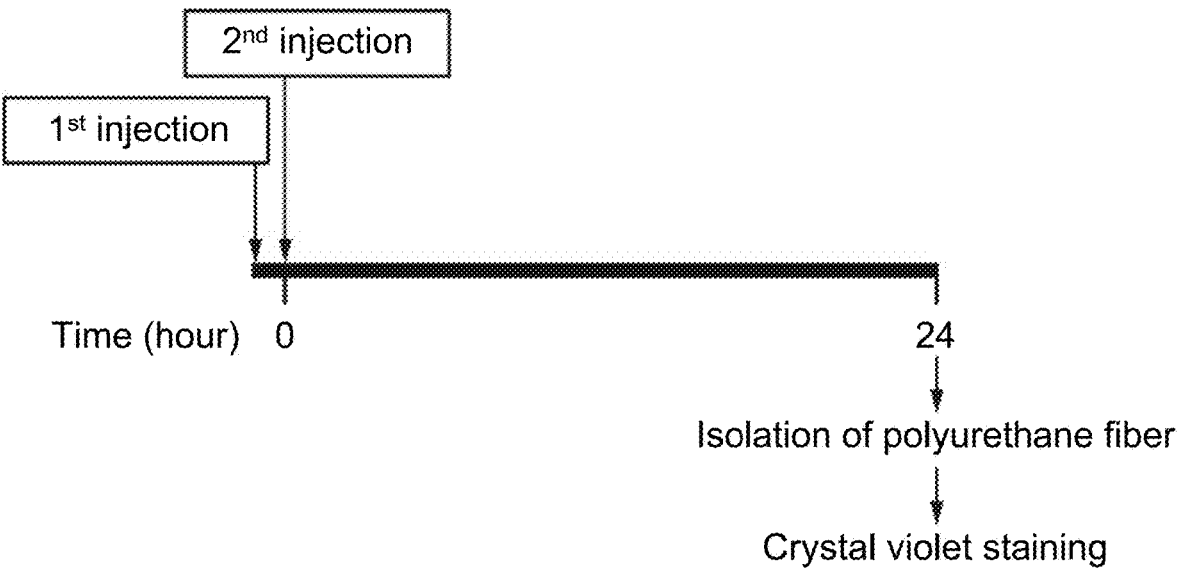
FIG. 11 illustrates an experiment flow of Test Example 4.

Next, the effects of antifungal drugs were examined. FIG. 11 illustrates the flow of an infection experiment. Then, 50 μl of physiological saline (saline) or a suspension of *C. albicans* strain SC5314 ($3 \times 10^7$ cells/ml) was inoculated into silkworms in which the polyurethane fibers were inserted. Immediately after the inoculation of *C. albicans,* 50 μl of 50 μg/ml amphotericin B (AMPH-B), 1.6 mg/ml fluconazole (FLCZ), or 1 mg/ml micafungin (MCFG) was inoculated into the humors of the silkworms as an antifungal drug. The polyurethane fibers were extracted from inside the bodies of the silkworms in the same way as in Test Example 3 after 24 hours, stained with crystal violet, and used for evaluation. The test was performed using seven samples in each group.

Figure 12:
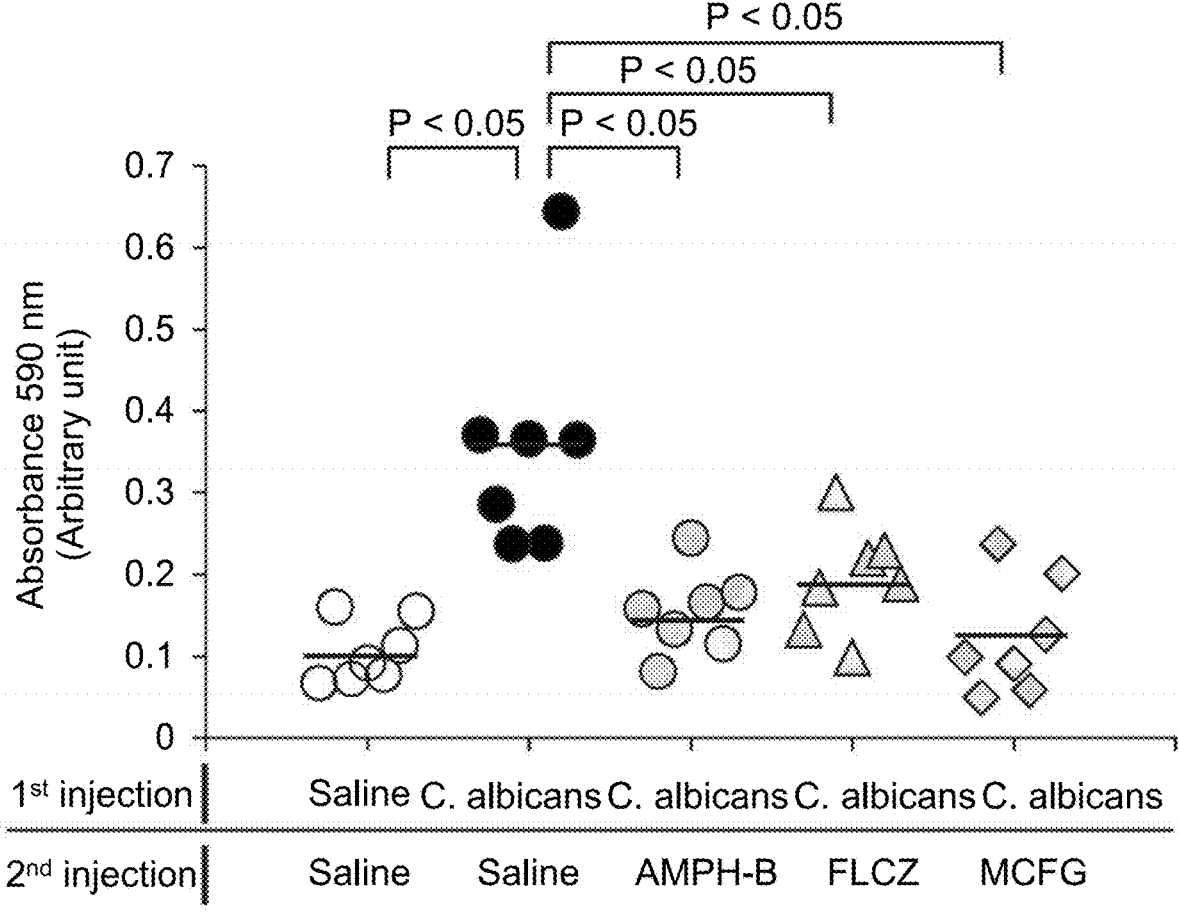
FIG. 12 illustrates results of Test Example 4.

FIG. 12 illustrates the results of the measured absorbances. When any of the antifungal drugs was administered to the silkworms inoculated with *C. albicans*, the biofilm formation on the polyurethane fibers in the bodies of the silkworms were significantly suppressed as compared with when physiological saline solution was inoculated into the silkworms inoculated with *C. albicans*.

[Test Example 5] (Suppression Effect of Antifungal Drugs on Biofilm Formation)

Figure 13:
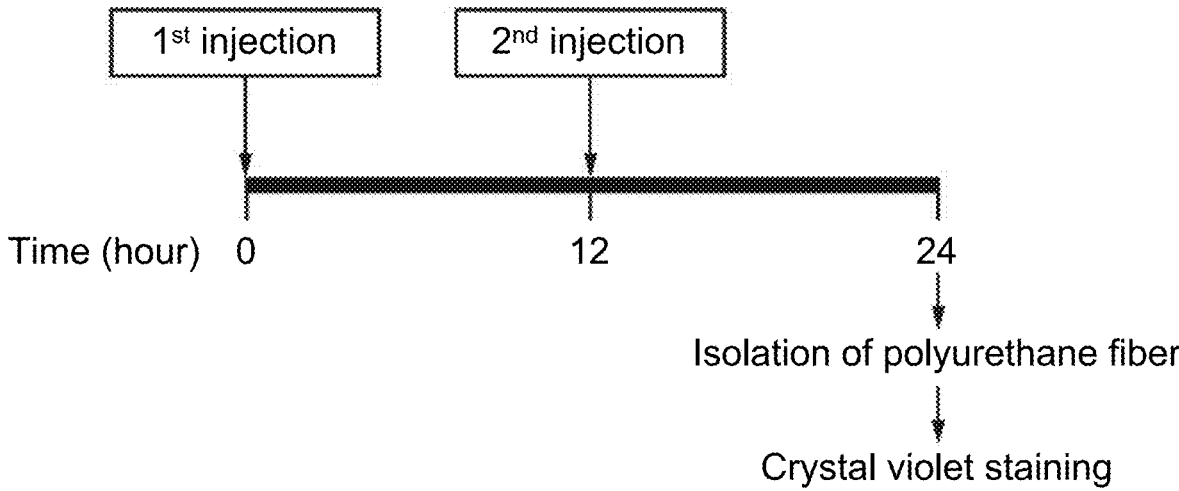
FIG. 13 illustrates an experiment flow of Test Example 5.

FIG. 13 illustrates the flow of the infection experiment of Test Example 5. In Test Example 5, physiological saline or *C. albicans* was first inoculated in the same way as in Test Example 4. Amphotericin B (AMPH-B), fluconazole (FLCZ), or micafungin (MCFG) was administered as an antifungal drug 12 hours after the inoculation *C. albicans*. The polyurethane fibers were extracted 24 hours after the inoculation of *C. albicans*. The extracted polyurethane fibers were stained with crystal violet and used for evaluation. The test was performed using six samples in each group.

Figure 14:
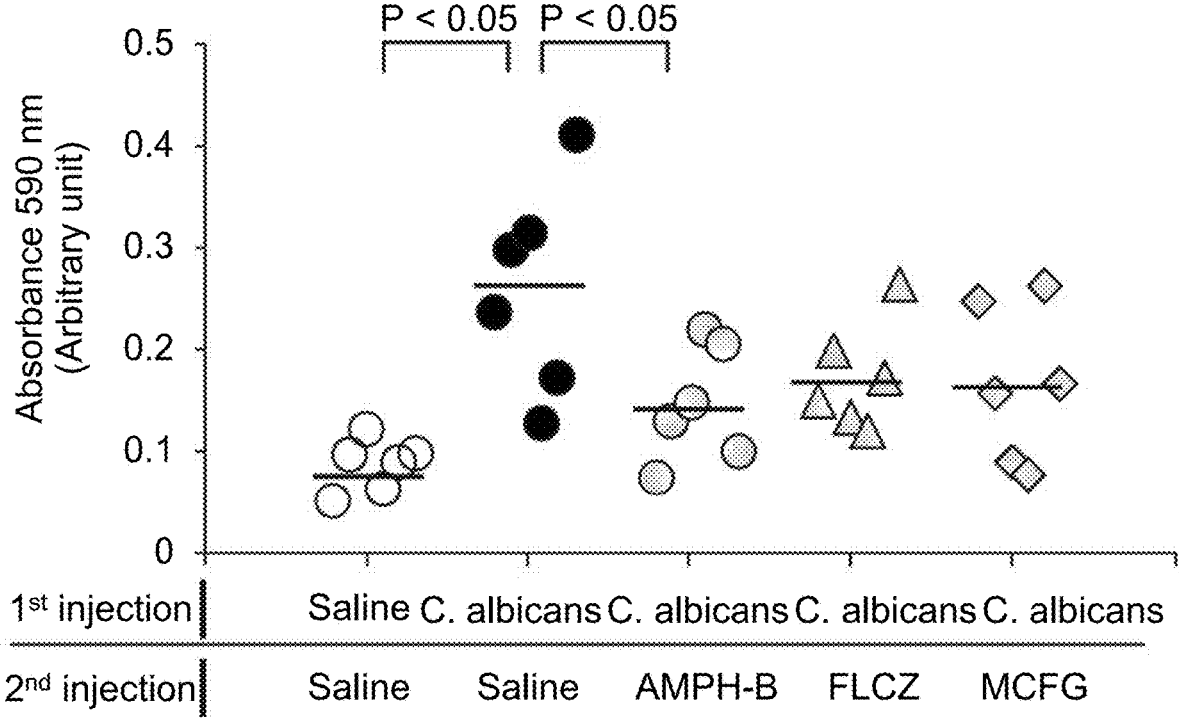
FIG. 14 illustrates results of Test Example 5.

FIG. 14 illustrates the results of the measured absorbances. When the antifungal drug was administered 12 hours after the inoculation of *C. albicans* into the silkworms, the biofilm formation on the polyurethane fiber in the bodies of the silkworms was significantly suppressed in the group to which amphotericin B was administered as compared with when physiological saline solution was inoculated 12 hours after *C. albicans* was inoculated into the silkworms.

[Test Example 6] (Suppression Effect of Antifungal Drug on Biofilm Formation)

Figure 15:
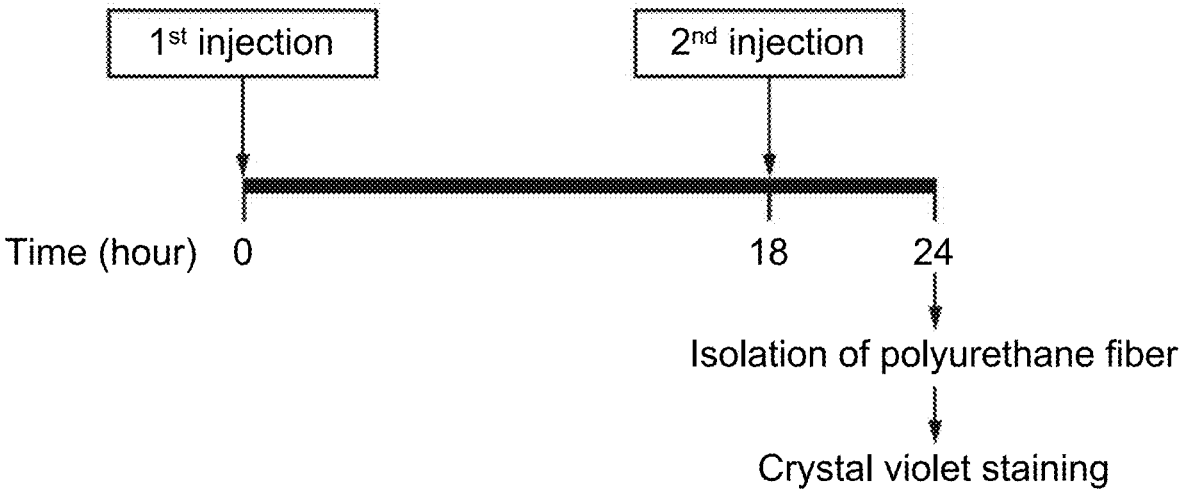
FIG. 15 illustrates an experiment flow of Test Example 6.

FIG. 15 illustrates the infection experiment flow of Test Example 6. In Test Example 6, physiological saline solution or *C. albicans* was first inoculated in the same way as in Test Example 4. Amphotericin B (AMPH-B), fluconazole (FLCZ), or micafungin (MCFG) was administered as an antifungal drug 18 hours after the inoculation of *C. albicans*. The polyurethane fibers were extracted 24 hours after the inoculation of *C. albicans*. The extracted polyurethane fibers were stained with crystal violet and used for evaluation. The test was performed using seven samples in each group.

Figure 16:
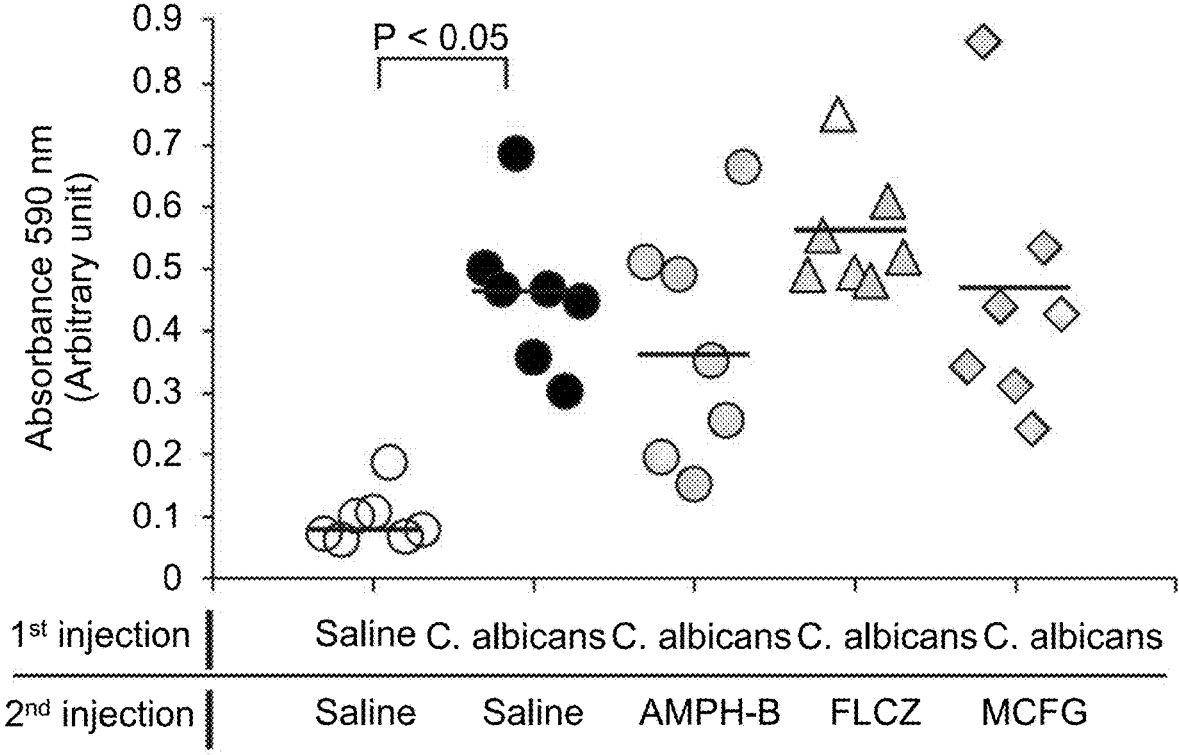
FIG. 16 illustrates results of Test Example 6.

FIG. 16 illustrates the results of the measured absorbances. When the antifungal drug was administered 18 hours after the inoculation of *C. albicans* into a silkworm, the biofilm formation on the polyurethane fibers in the bodies of the silkworms was not suppressed as compared with when physiological saline solution was inoculated 18 hours after *C. albicans* was inoculated into the silkworms.

It was suggested from the results of Test Examples 4 to 6 that although the suppression effect of the antifungal drug was seen in the early stage of the biofilm formation of *C. albicans* on the surface of the polyurethane fibers, the suppression effect of the antifungal drug was not seen in the late stage.

REFERENCE SIGN LIST

10: Silkworm, 12: Head, 14: Thorax, 16: Abdomen, 18: Intestinal Tract, 20: Crescent marking, and 30: Medical device material the invention claimed is:

1. A method comprising: a step of inserting a medical device material on a second segment from thorax side of abdomen between a hypodermal portion and the intestinal tract of a silkworm, through near a crescent marking on the abdomen of the silkworm; a step of extracting the medical device material from the silkworm; and a step of evaluating biofilm formation on a surface of the medical device material, by staining.

2. The method according to claim 1, comprising a step of infecting the silkworm in which the medical device material has been inserted with a fungus before the step of extracting the medical device material.

3. The method according to claim 1, comprising a step of administering an antimicrobial drug to the silkworm, wherein the step of evaluating the biofilm formation comprises evaluating the antimicrobial drug.

4. The method according to claim 1, wherein the medical device material is kept in the silkworm for a predetermined period of time after the medical device material has been inserted in the silkworm.

5. The method according to claim 1, wherein the medical device material forms a catheter as a medical device.

6. The method according claim 1, wherein the silkworm is a fifth instar silkworm.

7. The method according to claim 1, wherein a thickness of the medical device material is $\frac{1}{5}$ or less of a trunk thickness of the silkworm.

8. The method according to claim 1, wherein the medical device material is inserted along the intestinal tract of the silkworm in the step of inserting the medical device material.

* * * * *